United States Patent [19]

Roman

[11] 4,045,434

[45] Aug. 30, 1977

[54] ESTERS OF NITRO(TETRAHYDRO-2H-1,3-THIAZIN-2-YLIDENE)ACETIC ACIDS

[75] Inventor: Steven A. Roman, Oakdale, Calif.

[73] Assignee: Shell Oil Company, Houston, Tex.

[21] Appl. No.: 706,326

[22] Filed: July 19, 1976

[51] Int. Cl.$^2$ .......................................... C07D 279/06
[52] U.S. Cl. .................................. 542/413; 424/246; 542/427
[58] Field of Search ............ 260/240 R, 240 J, 240 A, 260/243 R

[56] References Cited

U.S. PATENT DOCUMENTS

| | | | |
|---|---|---|---|
| 3,962,225 | 6/1976 | Powell | 260/243 R |
| 3,962,233 | 6/1976 | Roman | 260/243 R |
| 3,962,234 | 6/1976 | Roman | 260/243 R |
| 3,981,871 | 9/1976 | Powell | 260/240 R |
| 3,985,736 | 10/1976 | Powell et al. | 260/243 R |
| 3,993,648 | 11/1976 | Powell | 260/243 R |

*Primary Examiner*—Arthur P. Demers

[57] ABSTRACT

Novel insecticidal esters of nitro(tetrahydro-2H-1,3-thiazin-2-ylidene)acetic acids.

3 Claims, No Drawings

ESTERS OF NITRO(TETRAHYDRO-2H-1,3-THIAZIN-2-YLIDENE)ACETIC ACIDS

DESCRIPTION OF THE INVENTION

It has been found that useful insecticidal activity is possessed by certain esters of nitro (tetrahydro-2H-1,3-thiazin-2-ylidene)acetic acids. These esters are resonance hybrids, the principal forms contributing thereto being described by the formula

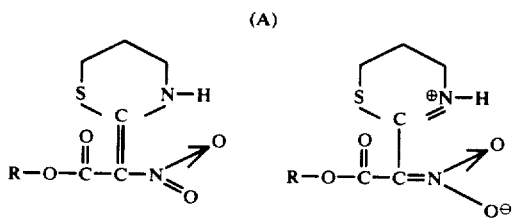

wherein R has the meaning set out hereinafter.

These compounds also can exist in the corresponding tautomeric enol form which can be described by the formula

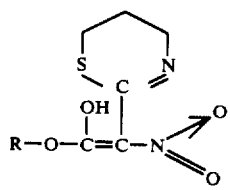

The resonance hybrids may exist as either of two geometric (cis-trans) isomers, depending upon the spatial relationship of the moieties about the bond between the carbon atom of the nitromethylene moiety and the ring carbon atom to which it is joined.

The enol form (Form C) can be designated as a 1-R-O-2-nitro-2-(5,6-dihydro-4H-1,3-thiazin-2-yl)vinyl alcohol. The left-hand form of the resonance hybrid (Form A) can be designated as an ester of nitro(tetrahydro-2H-1,3-thiazin-2-ylidene) acetic acid. The right-hand form (Form B) can be designated as an 2-(R-oxycarbonyl-aci-nitromethyl)-5,6-dihydro-4H-1,3-thiazinium hydroxide inner salt.

In this specification, for the sake of simplicity, these compounds will be referred to generally as esters of nitro(tetrahydro-2H-1,3-thiazin-2-ylidene)acetic acid. This terminology is intended to include all of the contributors to the resonance hybrid, the geometric isomers and the enol form, as well as mixtures thereof.

In these compounds, R represents the moiety

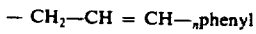

— $CH_2$—CH = CH—$_n$phenyl wherein n is one or two, and the phenyl moiety may be unsubstituted or substituted by from one to three of alkyl of from one to three carbon atoms, middle halogen (i.e., bromine or chlorine) or nitro.

For illustration, preparation of two typical species esters of the genus is described in the examples included hereinafter. Other typical illustrative species of this genus of esters include those wherein the symbol R represents the following moieties, this manner of naming these species being accurate, yet pointing out the differences between the different species more clearly than if the entire, complicated name of each species were to be given:

R = 3-(p-chlorophenyl)-2-propenyl;
3-(p-cumenyl)-2-propenyl;
3-(m-tolyl)-2-propenyl;
3-(2,4-xylyl)-2-propenyl;
5-(2,5-xylyl)-2, 4-pentadien-1yl;
3-(m-nitrophenyl)-2-propenyl;

Compounds of this invention can be prepared by the base-promoted transesterification of an alkyl ester of nitro(tetrahydro-2H-1,3-thiazine-2-ylidene)acetic acid (R = alkyl, for example, methyl or ethyl) which can be prepared by zinc ion-catalyzed reaction of 5,6-dihydro-2-(methylthio)-4H-1,3-thiazine (A. F. McKay et al., J. Am. Chem. Soc. 80, 3339 (1950)) with an alkyl nitroacetate (S. Zen, et al., Kogyo Kagaku Zasshi, 74, 70 (1971)).

The ester interchange follows the conventional catalyzed reaction of an ester with the alcoholate of the appropriate alcohol. The interchange can be effected by treating the appropriate 5-phenyl-2,4-pentadien-1-ol or 3-phenyl-2-propen-1-ol, in a solvent such as tetrahydrofuran or dimethylformamide, with an alkali metal hydride, then adding the ester, also in the solvent. The reaction of the alcohol and hydride usually is exothermic so that cooling is usually needed to control the temperature of the reaction mixture at 0°–10° C. Reaction of the alcoholate with the ester ordinarily can be conducted at room temperature.

Recovery of the product is most effectively attained in most cases by quenching the final reaction mixture in water, treating the aqueous mixture with a suitable solvent such as ether and/or methylene chloride, to remove the solvent alcohol and other neutral organic species, then acidifying the aqueous phase. In some cases, the product ester crystallizes out of the water; in other cases, it can be recovered by extracting the water-phase with a suitable water-insoluble solvent such as methylene chloride or ether.

Preparation of these compounds is illustrated in the following examples. In both cases, the identities of the products and of intermediates employed were confirmed by appropriate elemental and spectral analysis.

EXAMPLE 1

5-phenyl-2,4-pentadienyl nitro (tetrahydro-2H-1,3-thiazin-2-ylidene)acetate (1)

To a mixture of 221 g of 5,6-dihydro-2-(methylthio)-4H-1,3-thiazine (A. F. McKay et al., J. Am. Chem. Soc., 80, 3339 (1950) and 1 g of zinc chloride at about 100°, 202 g of methyl nitroacetate (S. Zen et al., Kogyo Kagaku Zasshi, 74, 70 (1971)) was added dropwise over a 30-minute period. The resulting mixture was heated for 4 hours at 95°–105°. 200 ml of isopropyl alcohol then was added to the hot mixture, then 400 ml of ether was added. The resulting mixture was filtered to give methyl nitro(tetrahydro-2H-1,3-thiazin-2-ylidene)-acetate (1A), as a pale yellow solid, m.p.: 107°–108° C.

A solution of 8.0 g of 5-phenyl-2,4-pentadien-1-ol in 30 ml of dimethylformamide (DMF) was added dropwise over a 30-minute period to a mixture of 1.5 g of sodium hydride and 20 ml of DMF, at 5°. The mixture was stirred for 1 hour at 5°. Then 3.3 g of 1A was added to the stirred mixture at 5° and the resulting mixture was stirred for three hours. The mixture then was poured into ice water and extracted with ether, and the aqueous phase was separated, acidified with acetic acid and extracted with methylene chloride. The methylene chloride extracts were washed with water, dried (MgSO$_4$), and stripped of solvent. The residue was triturated in water and then ether, to give a solid which on recrystallization from ethanol gave 1, as a yellow solid, m.p.: 123°–125°.

EXAMPLE 2

3-phenyl-2-propenyl nitro(tetrahydro-2H-1,3-thiazin-2-ylidene)acetate (2)

2 was prepared as a yellow solid, m.p.: 115°–116°, from 1A and cinnamyl alcohol by the procedures described in Example 1.

The compounds of this invention exhibit useful insecticidal activity, being of particular interest for control of the larvae "caterpillar" or "worm" forms of insects of the genus Heliothis, such as H. zea (corn earworm, cotton bollworm, tomato fruitworm), H. virescens (tobacco budworm); the genus Agrotis, such as A. ipsilon (black cutworm); the genus Trichoplusia, such as T. ni (cabbage looper), and the genus Spodoptera, such as S. littoralis (Egyptian cotton leafworm). One also is of interest for controlling aphids and houseflies. In tests that have been conducted both have exhibited low, or no, toxicity to other insects such as the 2-spotted spider mite and mosquito larva. One acts very rapidly on corn earworms, providing "quick knock-down" of these insects.

Activity of the compounds of this invention with respect to insects was determined by using standardized tests to establish the LC$_{50}$ dosage (in milligrams of test compound per 100 milliliters of solvent or liquid carrier required in the solution or suspension of test compound used) that was required to kill 50% of the test insects. The test insects were the housefly, corn earworm, mosquito, pea aphid and 2-spotted spider mite, and in some cases, the black cutworm.

Both of compounds 1 and 2 were found to be inactive or but slightly active with respect to the mites and mosquito larvae. Both were found to be highly active with respect to the corn earworm. Compound 2 was found to be active, with respect to the housefly and pea aphid.

In the course of these tests it was noted that compound 2 acted very quickly upon the corn earworms.

The invention includes within its scope insecticidal compositions comprising an adjuvant — that is, a carrier optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers; solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%W of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim as my Invention:

1. A resonance hybrid in which the significant forms are represented by the formulae

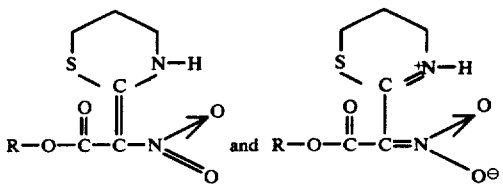

and the enol form represented by the formula

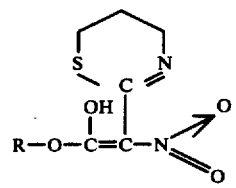

wherein R represents the moiety

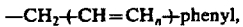

$n$ being one or two, and "phenyl" being the unsubstituted phenyl moiety or such substituted by from one to three of alkyl of from one to three carbon atoms, middle halogen or nitro.

2. A hybrid according to claim 1 wherein "phenyl" is the unsubstituted phenyl moiety and $n$ is 1.

3. A hybrid according to claim 1 wherein "phenyl" is the unsubstituted phenyl moiety and $n$ is 2.

* * * * *